United States Patent
Vail et al.

(10) Patent No.: US 10,101,263 B1
(45) Date of Patent: Oct. 16, 2018

(54) METHODS FOR EVALUATING SUPERABRASIVE ELEMENTS

(71) Applicant: US SYNTHETIC CORPORATION, Orem, UT (US)

(72) Inventors: Michael A. Vail, Genola, UT (US); Kenneth E. Bertagnolli, Riverton, UT (US); Jason K. Wiggins, Draper, UT (US)

(73) Assignee: US SYNTHETIC CORPORATION, Orem, UT (US)

( * ) Notice: Subject to any disclaimer, the term of this patent is extended or adjusted under 35 U.S.C. 154(b) by 380 days.

(21) Appl. No.: 14/557,154

(22) Filed: Dec. 1, 2014

Related U.S. Application Data

(60) Provisional application No. 61/912,831, filed on Dec. 6, 2013.

(51) Int. Cl.
   *G01N 19/04* (2006.01)
   *G01N 29/14* (2006.01)

(52) U.S. Cl.
   CPC ............ *G01N 19/04* (2013.01); *G01N 29/14* (2013.01)

(58) Field of Classification Search
   CPC ........... G01N 19/04; G01N 29/14; G01N 3/56
   USPC ................................................................ 73/7
   See application file for complete search history.

(56) References Cited

U.S. PATENT DOCUMENTS

| | | |
|---|---|---|
| 4,268,276 A | 5/1981 | Bovenkerk |
| 4,410,054 A | 10/1983 | Nagel et al. |
| 4,468,138 A | 8/1984 | Nagel |
| 4,560,014 A | 12/1985 | Geczy |
| 4,700,224 A * | 10/1987 | Miyasaka ............. B23Q 17/09 382/152 |
| 4,738,322 A | 4/1988 | Hall et al. |
| 4,811,801 A | 3/1989 | Salesky et al. |
| 4,913,247 A | 4/1990 | Jones |
| 5,016,718 A | 5/1991 | Tandberg |
| 5,092,687 A | 3/1992 | Hall |
| 5,120,327 A | 6/1992 | Dennis |
| 5,135,061 A | 8/1992 | Newton, Jr. |
| 5,154,245 A | 10/1992 | Waldenstrom et al. |
| 5,180,022 A | 1/1993 | Brady |
| 5,364,192 A | 11/1994 | Damm et al. |

(Continued)

FOREIGN PATENT DOCUMENTS

JP    2008151690 A  *  7/2008

OTHER PUBLICATIONS

Ando. Trnalsation of JP2008151690. Published Jul. 2008. Translated Oct. 2016.*
U.S. Appl. No. 61/912,831, filed Dec. 6, 2013, Vail et al.

*Primary Examiner* — Walter L Lindsay, Jr.
*Assistant Examiner* — Philip Marcus T Fadul
(74) *Attorney, Agent, or Firm* — FisherBroyles, LLP

(57) ABSTRACT

Embodiments of methods are disclosed for characterizing a tested superabrasive element, such as a polycrystalline diamond element. In an embodiment, a method of characterizing the relative strength of a superabrasive element is disclosed. A first superabrasive element and a second superabrasive element are positioned upper surface to upper surface, including an area of overlap between the upper surfaces. A load is applied while the first and second superabrasive elements are overlapped until failure of one or both of the first or second superabrasive elements fail. A relative strength is determined using at least the load during failure as a parameter.

22 Claims, 11 Drawing Sheets

(56) References Cited

U.S. PATENT DOCUMENTS

| | | | |
|---|---|---|---|
| 5,368,398 A | 11/1994 | Damm et al. | |
| 5,460,233 A | 10/1995 | Meany et al. | |
| 5,480,233 A | 1/1996 | Cunningham | |
| 5,544,713 A | 8/1996 | Dennis | |
| 6,793,681 B1 | 9/2004 | Pope et al. | |
| 7,866,418 B2 | 1/2011 | Bertagnolli et al. | |
| 7,998,573 B2 | 8/2011 | Qian et al. | |
| 8,034,136 B2 | 10/2011 | Sani | |
| 8,236,074 B1 | 8/2012 | Bertagnolli et al. | |
| 8,995,742 B1 * | 3/2015 | Cooley | G06T 7/0004 382/141 |
| 2009/0033644 A1 * | 2/2009 | Kawaguchi | G09G 3/3216 345/205 |
| 2010/0122567 A1 * | 5/2010 | Linares | G01N 3/56 73/7 |
| 2014/0250974 A1 * | 9/2014 | Gledhill | G01N 3/58 73/7 |
| 2016/0101600 A1 * | 4/2016 | Potts | B32B 27/285 428/419 |
| 2016/0215361 A1 * | 7/2016 | Yoon | B21B 3/00 |

\* cited by examiner

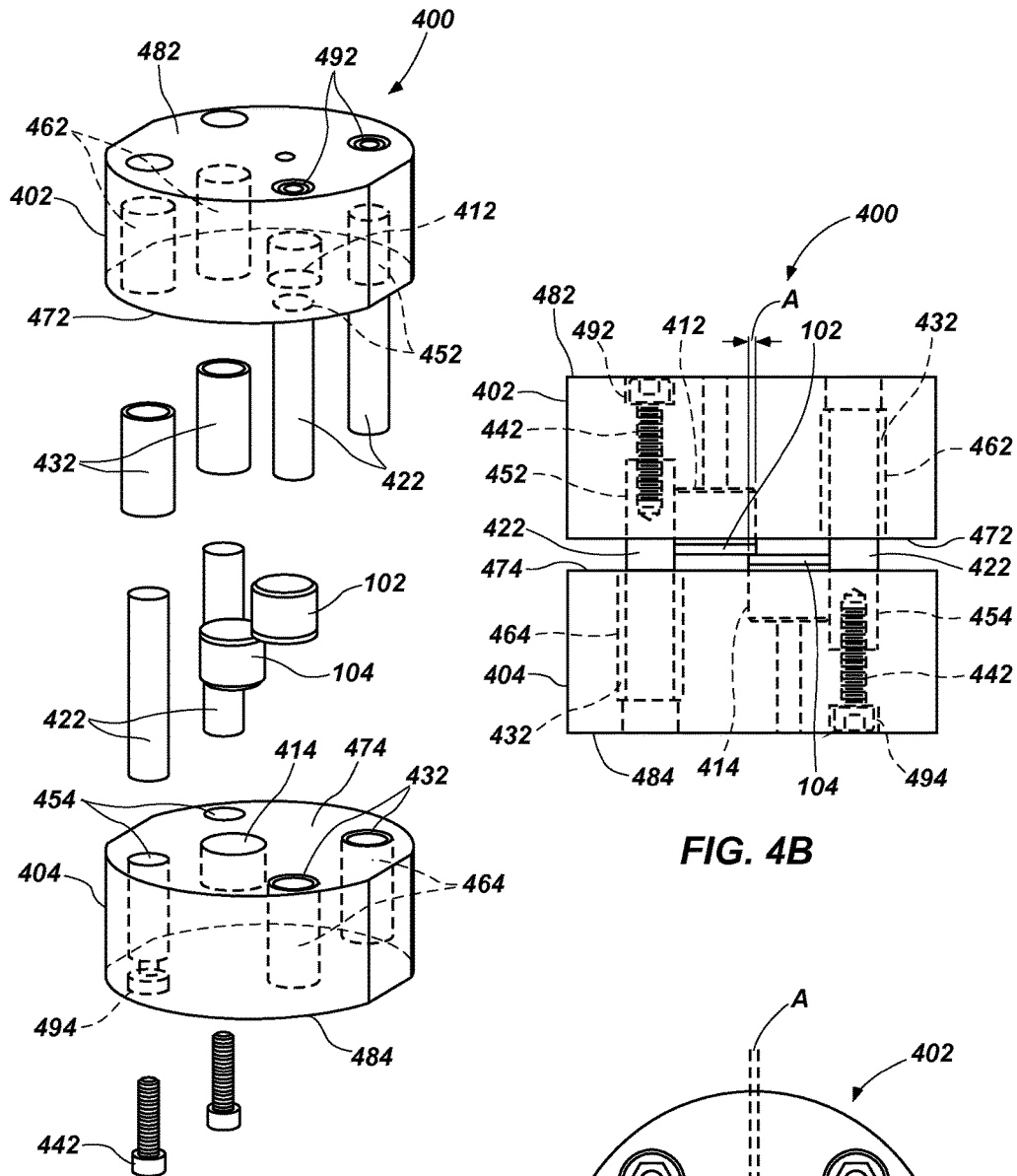

METHODS FOR EVALUATING SUPERABRASIVE ELEMENTS

CROSS-REFERENCE TO RELATED APPLICATIONS

This application claims priority to U.S. Provisional Patent Application No. 61/912,831 filed on 6 Dec. 2013, the disclosure of which is incorporated herein, in its entirety, by this reference.

BACKGROUND

Wear-resistant, polycrystalline diamond compacts ("PDCs") are utilized in a variety of mechanical applications. For example, PDCs are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller-cone drill bits and fixed-cutter drill bits. A PDC cutting element typically includes a superabrasive diamond layer commonly known as a diamond table. The diamond table is formed and bonded to a substrate using a high-pressure/high-temperature ("HPHT") process under diamond-stable conditions. The PDC cutting element may be brazed directly into a preformed pocket, socket, or other receptacle formed in a bit body. The substrate may often be brazed or otherwise joined to an attachment member, such as a cylindrical backing. A rotary drill bit typically includes a number of PDC cutting elements affixed to the bit body. It is also known that a stud carrying the PDC may be used as a PDC cutting element when mounted to a bit body of a rotary drill bit by press-fitting, brazing, or otherwise securing the stud into a receptacle formed in the bit body.

Conventional PDCs are normally fabricated by placing a cemented carbide substrate into a container or cartridge with a volume of diamond particles positioned on a surface of the cemented-carbide substrate. A number of such cartridges may be loaded into an HPHT press. The substrate(s) and volume(s) of diamond particles are then processed under HPHT conditions in the presence of a catalyst material that causes the diamond particles to bond to one another to form a matrix of bonded diamond grains defining a polycrystalline diamond ("PCD") table. The catalyst material is often a metal-solvent catalyst (e.g., cobalt, nickel, iron, or alloys thereof) that is used for promoting intergrowth of the diamond particles.

In one conventional approach, a constituent of the cemented carbide substrate, such as cobalt from a cobalt-cemented tungsten carbide substrate, liquefies and sweeps from a region adjacent to the volume of diamond particles into interstitial regions between the diamond particles during the HPHT process. The cobalt acts as a catalyst to promote intergrowth between the diamond particles, which results in formation of a matrix of bonded diamond grains having diamond-to-diamond bonding therebetween, with interstitial regions between the bonded diamond grains being occupied by the solvent catalyst. Accordingly, diamond grains become mutually bonded to form a matrix of PCD, with interstitial regions between the bonded diamond grains being occupied by the solvent catalyst.

The wear resistance and/or relative strength of the PCD table may depend on, by way of non-limiting example, one or more of the size or shape of the interstitial regions between the bonded diamond grains, the thickness of the PCD table, the proportion of PCD table to substrate thickness, sintering pressure, sintering temperature, the composition of the PCD table, or metal-solvent catalyst content.

Therefore, manufacturers and users of PDCs have a need to accurately characterize the mechanical properties of PDCs.

SUMMARY

Embodiments of the invention relate to methods for measuring at least one failure characteristic of a superabrasive element (e.g., a PCD element or table) under load and, for example, using the measurement to characterize a relative strength of the superabrasive element and/or for quality control on such a superabrasive element. Measurement of at least one failure characteristic may be used to characterize a relative strength of a superabrasive element and/or adjust process parameters for fabricating a superabrasive element based on additional characteristics, such as, by way of non-limiting example, superabrasive element thickness, superabrasive table to substrate proportion, superabrasive element density, superabrasive element porosity, diamond grain size, metal-solvent catalyst composition, nonmetallic catalyst composition, sintering temperature, sintering pressure, leaching, leaching time, leaching agent composition, leaching agent concentration, or combinations thereof.

In an embodiment, a method for characterizing a superabrasive element is disclosed. The method includes positioning a first superabrasive element having a first upper surface and a second superabrasive element having a second upper surface so that the first and second upper surfaces of the first and second superabrasive elements are at least partially overlapping and facing each other to define an area of overlap therebetween. The method includes loading the first superabrasive element and second superabrasive element against each other while overlapped. The method includes observing at least one event in either one or both of the first or second superabrasive elements during the act of loading. The method further includes characterizing the relative strength of one or both of the superabrasive elements based at least partially on the at least one event.

In an embodiment, a method of characterizing a relative strength of a PCD element is disclosed. The method includes positioning a first PCD element having a first upper surface and a second PCD element having a second upper surface so that the first and second upper surfaces of the first and second PCD elements are at least partially overlapping and facing each other to define an area of overlap therebetween, at least one of the first or second PCD elements including a substrate and a PCD table bonded thereto. The method includes loading the first PCD element and second PCD element against each other while overlapped with a compressive load. The method includes observing at least one event in either one or both of the first or second PCD elements during the act of loading. The method further includes characterizing the relative strength of one or both of the PCD elements based at least partially on one or more observations made during at least one event.

In an embodiment, a method of characterizing a relative strength of a superabrasive compact element is disclosed. The method includes positioning a first superabrasive element having a first upper surface and a second superabrasive element having a second upper surface so that the first and second upper surfaces of the first and second superabrasive elements are overlapping and facing each other to define an area of overlap therebetween. The method includes applying a compressive load to the first superabrasive element and second superabrasive element while overlapped. The method includes producing at least one event in one or both superabrasive elements during the act of applying a compressive load. The method includes sensing at least one light emission produced during application of the compressive load using a light detecting array and sensing an applied load during the at least one light emission. The method further includes characterizing the relative strength of one or both superabrasive elements at least partially based on the at least one light emission and the applied load corresponding thereto.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

FIG. 4A is an exploded isometric view of a fixture configured to limit movement of the first and second superabrasive elements according to an embodiment.

FIG. 4B is a side view of the assembled fixture of FIG. 4A.

FIG. 4C is a top plan view of the fixture of FIG. 4B.

DETAILED DESCRIPTION

Embodiments disclosed herein are generally directed to methods for characterizing a superabrasive element. Embodiments include observing and/or measuring at least one indicia of a failure of a superabrasive element (e.g. a superabrasive table) under load (e.g., compressive load) and using the observations and/or recorded measurement(s) to characterize a relative strength of the superabrasive element and/or for quality control. For example, the observed and/or recorded indicia of failure may be used to determine if the superabrasive element is suitable for use in a subterranean drilling apparatus. Observed and/or recorded data of the indicia of failure may be used to characterize the relative strength of the superabrasive element and/or adjust process parameters for fabricating the superabrasive element.

In an embodiment, the relative strength of a given superabrasive element may be correlated to processes used to manufacture the given superabrasive element and/or other superabrasive element characteristics such as, by way of non-limiting example, superabrasive element thickness, superabrasive table to substrate proportion, superabrasive element density, superabrasive element porosity, diamond particle grain size, metal solvent catalyst composition, non-metallic catalyst composition, sintering temperature, sintering pressure, use of leaching, leaching time, leaching agent composition, leaching agent concentration, or combinations thereof.

Figure 1A:
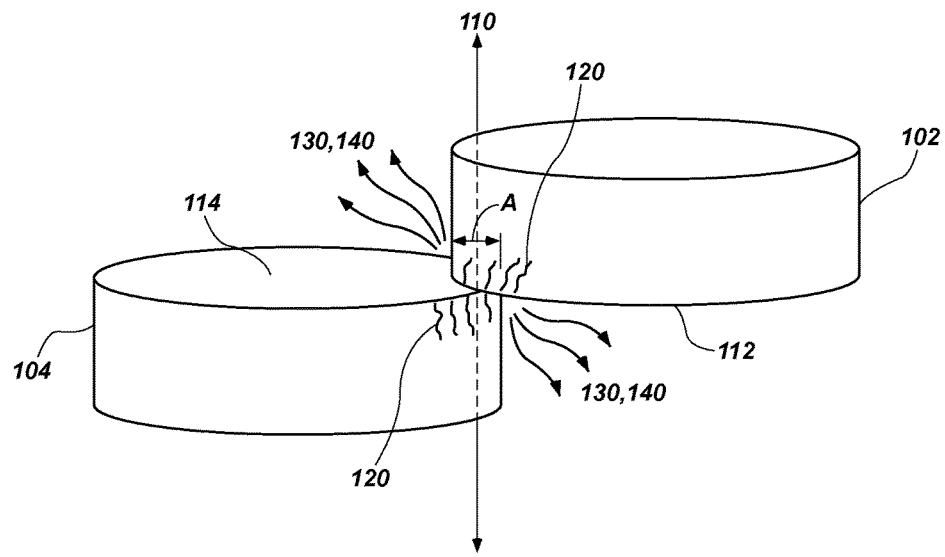
FIG. 1A is an isometric view of first and second superabrasive elements under compressive load according to an embodiment.

Embodiments of Methods for Characterizing a Relative Strength of a Superabrasive Element FIG. 1A illustrates an embodiment of superabrasive elements generally opposing and overlapping each other under load (e.g., compressive load). In an embodiment, a first superabrasive element 102 and a second superabrasive element 104 are manufactured with the same or substantially the same processes and/or exhibit the same or substantially similar geometry. A first superabrasive element 102 having an upper surface 112 is generally opposed to a second superabrasive element 104 having an upper surface 114, with the upper surfaces 112 and 114 overlapping each other to define an overlap area A. An axis of loading 110 is located in or near a center of the area of overlap A such that an applied load (e.g., compressive load) is located generally in the center of the area of overlap A between the upper surfaces 112 and 114 of the superabrasive elements 102 and 104. A load is applied to the superabrasive elements 102 and 104 until one or both of the superabrasive elements 102 and 104 exhibit one or more selected indicia of failure (e.g., failure event criteria) or another selected evaluation criteria.

Figure 1B:
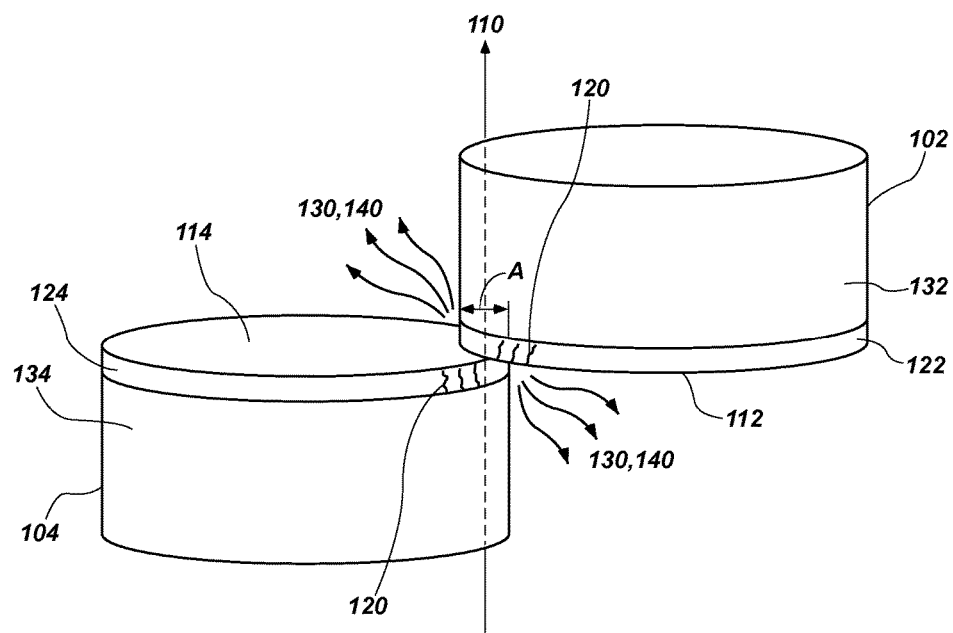
FIG. 1B is an isometric view of first and second superabrasive elements having a substrate and a superabrasive table, under compressive load, according to an embodiment.

Evaluation or observation of a superabrasive element may occur or be defined at a single point in time, by a single indicator, over a period of time or varying conditions (e.g., force or duration of applied load), and/or by more than one indicator or indicia. The one or more indicia may be evidence of a discrete failure event (e.g., cracking, spalling, separation from a substrate, delamination, etc.) or damage accumulation (singly or collectively, an "event") in one or more superabrasive elements under load. An event may be evidenced by one or more indicia or series of one or more indicia (e.g., over a discrete duration or applied force). For example, indicia of an event may include cracking 120 that is visible, acoustic emission(s) 130, emission(s) of energy (e.g., light) 140, or combinations thereof. Observed and/or recorded indicia may provide evidence of an event in one or both superabrasive elements 102 and 104. Cracking 120 may, typically, be in the form of so-called "thumb nail cracks" or other crack geometry commonly exhibited during failure of a PCD element in compressive loading configurations. Although cracking 120 is illustrated in FIGS. 1A, 1B, and 5B as visual features, cracking 120 may be hidden, embedded, not visible, or otherwise difficult to detect. In an embodiment, an event may be evidenced by spalling or separation of smaller portions of the superabrasive element from the main body of the superabrasive element 102 or 104. In an embodiment, an event or series of events may occur during any discrete portion of, or, over a duration of the entire process of loading.

In an embodiment, a superabrasive element 102 and/or 104 may include, without limitation, polycrystalline diamond, cubic boron nitride, silicon carbide, carbon nitride, other carbides exhibiting a hardness at least equal to that of tungsten carbide, or any combination of the foregoing. For example, in an embodiment, the superabrasive element 102 and/or 104 may comprise polycrystalline diamond.

FIG. 1B illustrates an embodiment of superabrasive elements generally opposing and overlapping each other under load. In the illustrated embodiment, the superabrasive elements may include a substrate and a superabrasive table bonded to the substrate. For example, the first superabrasive element 102 includes a first superabrasive table 122 and a first substrate 132 bonded together along an interface 142, with the first superabrasive table 122 defining the upper surface 112 of the first superabrasive element 102. In an embodiment, the second superabrasive element 104 includes a second superabrasive table 124 and a second substrate 134 bonded together along an interface 144, with the second superabrasive table 124 defining the upper surface 114 of the first superabrasive element 104.

Figure 1C:
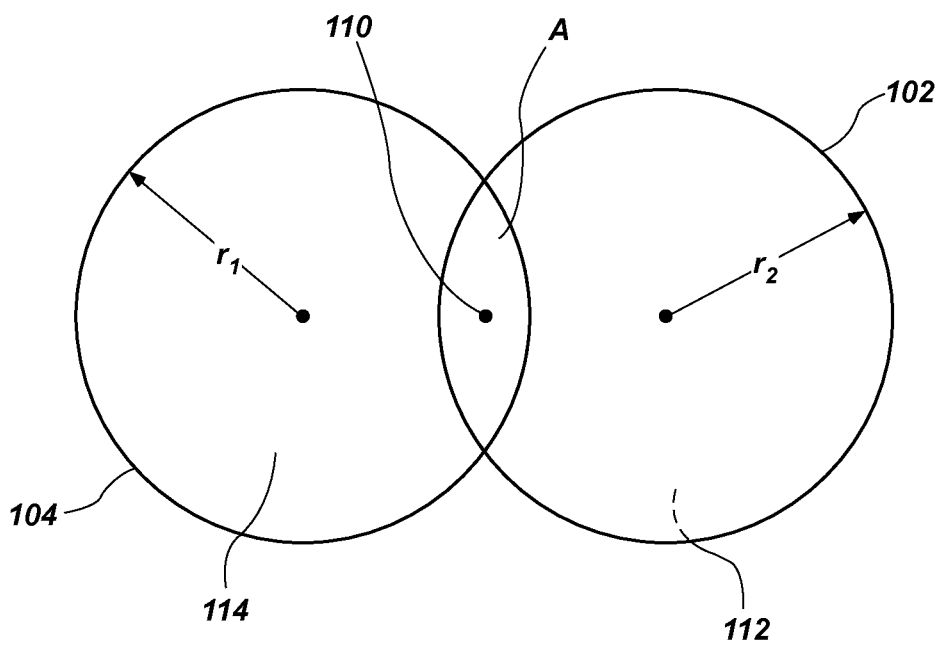
FIG. 1C is a top plan view of the first and second superabrasive elements of FIG. 1B.

As shown in FIG. 1C, the axis of loading 110 is located generally in the center/centroid of the area overlap A such that an applied load is located substantially in the center/centroid of the area of overlap A between the upper surfaces 112 and 114 of the superabrasive elements 102 and 104. In an embodiment, the center/centroid of the area of overlap A between two round superabrasive elements 102 and 104 may be defined by the radii $r_1$ and $r_2$ of the respective superabrasive elements. In such an embodiment, the area of overlap A and by extension thereof, the center/centroid of the area of overlap A defining where the axis of loading 110 is substantially located, is a function of the relationship between the overlap of the two radii $r_1$ and $r_2$. For example, the area of overlap A and centroid therein may be defined by a formula for determining a center of the area of overlap between two circles. By way of another non-limiting example, a center of the area of overlap A of two overlapping substantially rectangular superabrasive elements having a substantially rectangular area of overlap A may be determined using a simple formula for an area of a rectangle. Although embodiments of superabrasive elements shapes are depicted as circular, many shapes of superabrasive elements 102 and/or 104 are contemplated herein, including matching and non-matching; circular shapes, round shapes (e.g. oval), quadrilateral shapes (e.g., square, rectangle, rhombus, or trapezoid), triangular shapes, many sided shapes, irregular shapes, and combinations thereof. Further, calculating the area of overlap A and by extension thereof the center/centroid defining the axis of loading 110, may be carried out using any known techniques.

In an embodiment, a load is applied to the superabrasive elements 102 and 104 until an event (e.g., failure event or damage accumulation) occurs, as disclosed herein. Such an event may include, but not be limited to, partial (e.g., limited cracking or spalling) or total failure (e.g., spalling of substantially all or large portions (e.g., 50% or more) of the overlapped area A of one or more of the superabrasive elements. In an embodiment, an event may be evidenced by a portion of the superabrasive table 122 and/or 124 separating from the substrate 132 and/or 134 respectively.

In an embodiment, the superabrasive table 122 and/or 124 may include, without limitation, polycrystalline diamond, cubic boron nitride, silicon carbide, carbon nitride, other carbides exhibiting a hardness at least equal to that of tungsten carbide, or any combination of the foregoing. For example, in an embodiment, the superabrasive table 122 and/or 124 includes polycrystalline diamond.

In an embodiment, the substrate 132 and/or 134 may include without limitation, cemented carbides, such as tungsten carbide, titanium carbide, chromium carbide, niobium carbide, tantalum carbide, vanadium carbide, or combinations thereof cemented with iron, nickel cobalt, other metals, or alloys thereof. In an embodiment, the substrate 132 and/or 134 includes cobalt-cemented tungsten carbide. In an embodiment, the superabrasive table 122 and/or 124 includes sintered polycrystalline diamond and the substrate 132 and/or 134 comprises a cobalt-cemented tungsten carbide. Examples of methods for fabricating the superabrasive elements 102 and 104 and the resultant superabrasive elements are disclosed in U.S. Pat. Nos. 7,866,418; 7,998,573; 8,034,136; and 8,236,074, the disclosure of each of the foregoing patents is incorporated herein, in its entirety, by this reference.

In an embodiment, the first superabrasive element 102 and the second superabrasive element 104 may be manufactured in the same way or a substantially similar way with the same or substantially the same materials. The first superabrasive element 102 and the second superabrasive element 104 may exhibit the same or substantially similar geometry. In an embodiment, at least the load applied during one or more events may be measured, observed, or recorded. In an embodiment, the displacement of the superabrasive elements during loading including any events resulting therefrom may be measured, observed, or recorded. In an embodiment, acoustic emissions produced during one or more events may be recorded using an acoustic sensor. In an embodiment, one or more events may be recorded using a high speed camera or optical sensor to record visual data (e.g., images or light emissions) during the one or more events. In an embodiment, one or more emissions of light produced during one or more events may be recorded using a light detecting array.

Figure 2:
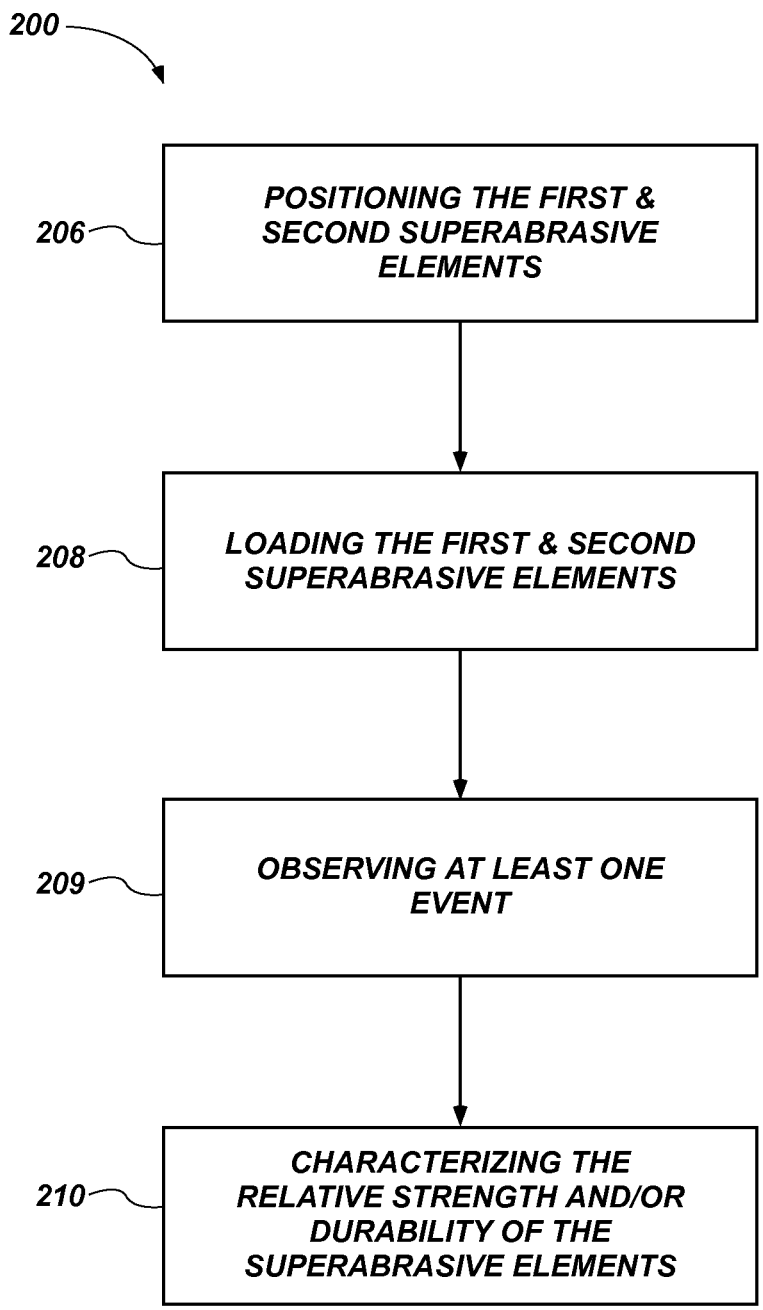
FIG. 2 is a flow diagram illustrating a method for characterizing a relative strength of a superabrasive element according to an embodiment.

FIG. 2 illustrates a method 200 for characterizing a superabrasive element according to an embodiment. The method 200 includes an act 206 of positioning a first superabrasive element 102 having an upper surface 112 and a second superabrasive element 104 having an upper surface 114 such that the upper surfaces 112 and 114 are opposing each other and at least partially overlap. The method 200 further includes an act 208 of loading (e.g., compressive load) the superabrasive elements 102 and 104, while overlapped with each other, until at least one event occurs (e.g., one or more failure events or damage accumulation occurs). The method includes the act 209 of observing at least one event, which may include at least one of observing, detecting, sensing, or recording the at least one event. The method further includes the act 210 of characterizing a relative strength and/or durability of one or both superabrasive elements 102 and 104 at least partially based on a maximum applied load during the test (e.g., the compressive load causing fracture or complete failure of at least a portion of superabrasive element 102 and/or 104). In an embodiment, the overlap area A between the upper surfaces 112 and 114 of the superabrasive elements 102 and 104 may additionally be used to characterize a relative strength of one or both superabrasive elements 102 and/or 104. The relative strength of the superabrasive elements may be calculated by taking a ratio of a load applied during the test (e.g., the maximum load) by the area of overlap A. The larger the calculated value, the larger the relative strength or durability of the superabrasive element.

The act of positioning 206 may include positioning the upper surface 112 of the first superabrasive element 102 to generally oppose the upper surface 114 of the second superabrasive element 104, wherein the upper surface 112 of the first superabrasive element 102 at least partially overlaps the upper surface 114 of the second superabrasive element 104, wherein the upper surfaces 112 and 114 are substantially parallel to each other. In an embodiment, the act 206 may include positioning the upper surface 112 of the first superabrasive element 102 so that it is angled at least more than zero degrees (0°) and less than ninety degrees (90°) with respect to the upper surface 114 of the second superabrasive element 104. In an embodiment, the superabrasive elements 102 and 104 may exhibit substantially equal elastic moduli, different elastic moduli, substantially equal failure strengths, different failure strengths, or combinations thereof. In an embodiment, the first superabrasive element 102 and the second superabrasive element 104 may be manufactured in the same way or a substantially similar way, or with the same or substantially the same materials. The first superabrasive element 102 and the second superabrasive element 104 may exhibit the same or substantially similar geometry. The load employed in act 208 may be a compressive load. In an embodiment, the load may increase linearly with respect to time, increase to a certain amount and remain constant thereafter, be cyclical (e.g., repeatedly rising and falling loads), combinations of the foregoing, or any other load applied by any suitable loading technique or pattern. In an embodiment, the loading technique may further include, placing the superabrasive elements 102 and 104 under compressive load, over a smaller or larger overlap area A in relation to previous samples, until one or more events are observed or until one or more of the superabrasive elements 102 or 104 completely fail or fracture (e.g., one or more of the overlapped portions completely spalling, delaminating or otherwise failing under stress).

In an embodiment of the act of positioning 206, the superabrasive elements 102 and 104 may be positioned in one or more fixtures such that the upper surface 112 of the first superabrasive element 102 generally opposes the upper surface 114 of the second superabrasive element 104. In such embodiments, the upper surface 112 of the first superabrasive element 104 overlaps an area A of the upper surface 114 of the second superabrasive element 104, and the one or more fixtures constrain movement of the superabrasive elements to the direction of the axis of loading 110 (e.g., parallel to the axis of loading). In an embodiment, the axis of loading 110 may be located in the center/centroid of the area of overlap A in order to constrain bending or deflection forces. The one or more fixtures may be mounted in a load frame or other suitable compressive testing apparatus. The load frame may then be used to load the superabrasive elements until or more events occur. For example, a MTS Landmark 500 kN Servo-hydraulic Load Frame may be employed in any of the embodiments disclosed herein.

In an embodiment, a superabrasive element may be positioned opposite a standard (e.g., standard superabrasive element or block of material); against which all tested superabrasive elements may be tested or compared. In such an embodiment, direct comparison of load strengths and/or load durations at failure or event(s) between differing superabrasive elements may indicate relative strength or durability of a superabrasive element. The superabrasive elements and/or the standard (e.g., polycrystalline diamond, tungsten carbide, or Barre granite) may be used in substantially the same or an identical manner as any of the superabrasive elements opposed to superabrasive elements disclosed herein.

In an embodiment, the act of loading 208 may include applying a fixed constant load to one or more superabrasive elements. In an embodiment, the act of loading 208 may include applying a ramping load at a selected rate. In an embodiment, the act of loading 208 may include applying a cyclic load. In an embodiment, the total load, rate of loading, rate of cycling the load, or combinations thereof may be higher or lower depending on the desired results or test data. For example, a relatively slower load rate may provide for better separation or distinction of individual cracking, acoustic emissions, or other indicia of events over a duration of time.

In an embodiment, the act 209 of observing at least one event may at least partially include observing and/or recording the load during an event. In an embodiment, the act 209 of observing at least one event may at least partially include observing and/or recording the maximum load applied during the act of loading 208. In an embodiment, the act 209 of observing one or more events may optionally include one or more of sensing and recording acoustic data (e.g., acoustic emissions) produced by one or both of the superabrasive elements during an event with an acoustic sensor, and/or recording visual changes (e.g., cracking) in the superabrasive elements during an event using an optical sensor. An embodiment may include an act of correlating (e.g., synchronizing) the acoustic data with the visual data to characterize or correlate the acoustic emissions produced during an event to at least one of a fracture, cracking, or other indicia of an event. An embodiment may include correlating the acoustic data and the visual data to the load data produced during an event. In an embodiment, the act 210 of characterizing the relative strength and/or durability of a superabrasive element based at least on load at or during failure may include using the acoustic data to characterize the relative strength of one or both superabrasive elements.

In an embodiment, the act 209 of observing at least one event (e.g., observing electromagnetic radiation, visible light, infrared light, ultraviolet light, beta particles, x-rays, combinations thereof, or any radiation emitted during an event) may optionally include sensing and recording emissions of energy produced from one or both superabrasive elements during an event using a detector (e.g., light-detecting array). In an embodiment, the act 210 of characterizing the relative strength and/or durability of one or both superabrasive elements based at least partially on the load applied may include using the sensed or recorded energy emission data to characterize the relative strength of one or both superabrasive elements.

In an embodiment, the act 206 of positioning a first superabrasive element having an upper surface and a second superabrasive element having an upper surface may additionally include coating one or both of the superabrasive elements in a photo-elastic coating material. The act 209 of observing at least one event may additionally include one or more of sensing, recording, or analyzing, in situ, the effect of the load on the photo-elastic coating of one or both superabrasive elements. The act 210 of characterizing the relative strength and/or durability of one or both superabrasive elements may additionally include characterizing the relative strength or durability of one or both superabrasive elements using at least the data collected from the analysis of the photo-elastic coatings under load.

In an embodiment, the act of characterizing the relative strength and/or durability of one or both superabrasive elements may include making the characterization at least partially based on the duration of time it takes to create an event, number of events, or complete failure; the load it takes to create an event, number of events, or complete failure; or combinations thereof. For example, a superabrasive element may be characterized as stronger based on requiring a larger load or a longer time under load to create an event or complete failure in one or more superabrasive elements.

Figure 3:
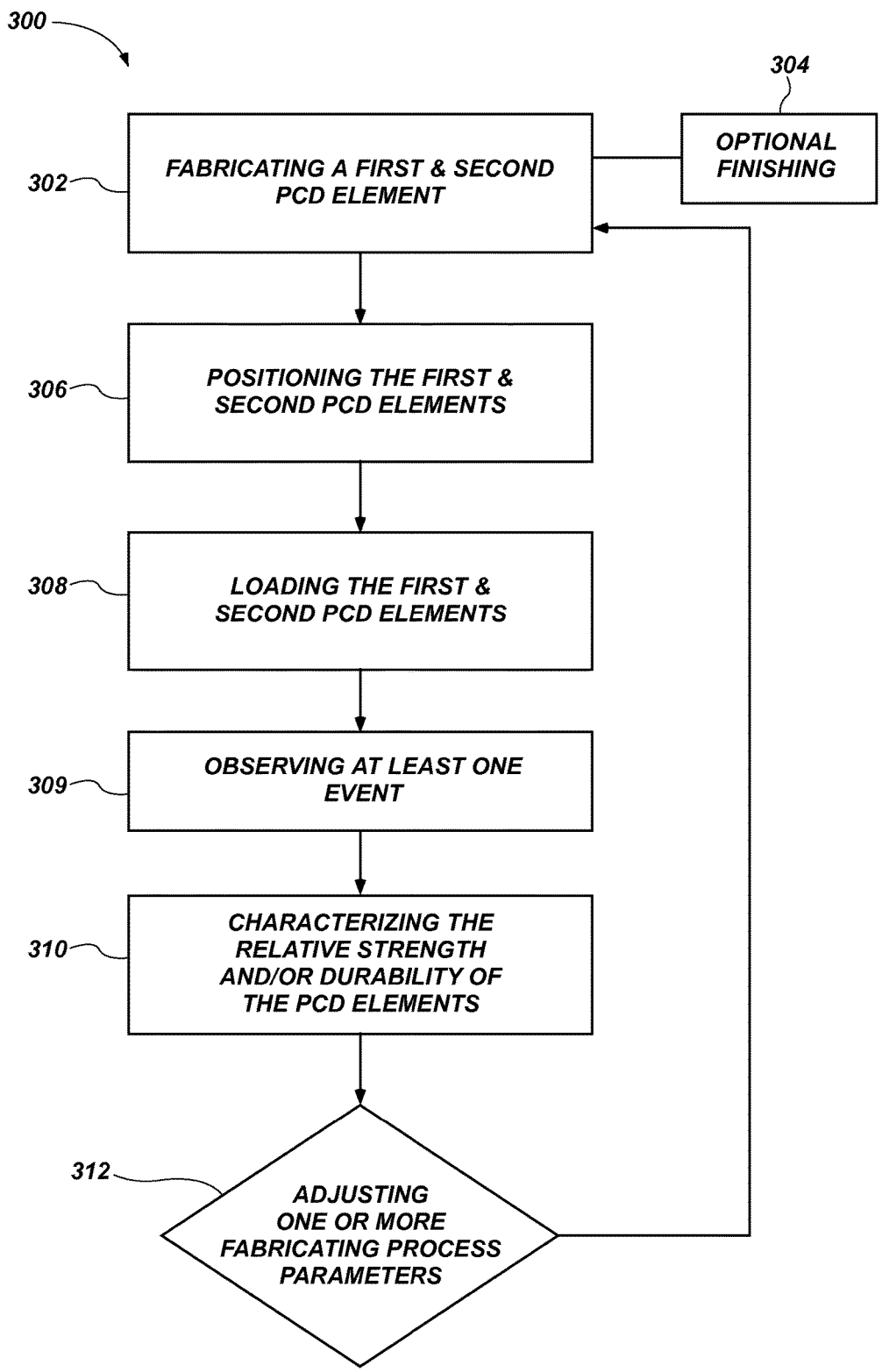
FIG. 3 is a flow diagram illustrating a method for adjusting one or more of the process parameters used in a method of manufacturing a superabrasive element according to an embodiment.

Referring now to FIG. 3, a method 300 for adjusting one or more process parameters used in fabrication of a superabrasive element responsive to the characterized or determined relative strength of the superabrasive element is illustrated according to an embodiment. The superabrasive element of the method 300 may include a PCD element, such as a PDC. The method 300 includes an act 302 of fabricating a PCD element. The act 302 of fabricating a PCD element may include providing a diamond powder and a catalyst, and subjecting the diamond powder and the catalyst to an HPHT process. After subjecting the diamond powder and catalyst to an HPHT process, optionally, one or more surfaces of the PCD element may be at least partially finished using techniques such as, but not limited to, lapping, centerless grinding, machining (e.g., electro-discharge machining), or combinations of the forgoing finishing processes. For example, the PCD element may be shaped to a selected geometry, such as shaping the PCD element to form a disk with an edge chamfer. In an embodiment, the act 302 of fabricating a PCD element may include, after either the HPHT sintering process or the finishing process, at least partially leaching the PCD element to form an at least partially leached PCD element. Leaching may be used to at least partially remove metal-solvent catalyst that was used to catalyze formation of diamond-to-diamond bonds in the PCD element. The at least partially leached PCD element may include a plurality of bonded diamond grains defining a plurality of interstitial spaces or pores extending therethrough. It should be noted that as an alternative or in addition to performing the finishing process prior to leaching, finishing may also be performed after leaching.

In an embodiment, the superabrasive element 102 or 104 may include a PCD table 122 or 124 bonded to a substrate 132 or 134 as shown in FIG. 1B. Optionally, the first superabrasive element 102 and the second superabrasive element 104 may be substantially similar, such as manufactured with identical processes or substantially similar processes and/or with the same or substantially similar materials. In an embodiment, the first superabrasive element 102 and the second superabrasive element 104 may exhibit identical or substantially similar geometry. In an embodiment, the act 302 of fabricating (or providing) a PCD element may include providing a diamond powder, with or without a metal solvent catalyst therewith. The diamond powder may exhibit one or more average diamond particle sizes or modes. In an embodiment, the act 302 of fabricating a PCD element may include providing a substrate which may further include a metal-solvent catalyst therein. In an embodiment, the act 302 of fabricating a PCD element may include subjecting the diamond powder and the substrate to a HPHT process wherein the metal-solvent catalyst in the substrate may infiltrate the mass of diamond powder to promote growth between adjacent diamond particles to form the PCD element. For example, cobalt from a cobalt-cemented tungsten-carbide substrate may be liquefied and infiltrate the mass of diamond particles to catalyze formation of the PCD element. Infiltration of the metal-solvent catalyst also provides bonding between the substrate and the resulting PCD table upon cooling. After subjecting the diamond powder and catalyst to an HPHT process, optionally, one or more surfaces of the PCD element and/or substrate may be at least partially finished using techniques such as but not limited to, lapping, centerless grinding, machining (e.g., electro-discharge machining), lasing, or combinations of the foregoing finishing processes. For example, the PCD element may be shaped to a selected geometry, such as shaping the PCD element to form a disk with an edge chamfer. The act 302 of fabricating a PCD element may include, after either the HPHT process or the finishing process, at least partially leaching the PCD element to form an at least partially leached PCD element. It should be noted that as an alternative or in addition to performing the finishing process prior to leaching, finishing may also be performed after leaching. Embodiments of PCD elements and methods of making the same used herein may include any of the specific HPHT sintering process conditions and/or the composition of the diamond powders or substrates described in U.S. Pat. Nos. 7,866,418; 7,998,573; 8,034,136; and 8,236,074, which have been incorporated herein by previous reference.

The method of 300 further includes an act 306 of positioning a first PCD element 102 and a second PCD element 104 substantially as described above regarding the act of positioning 206 of the method 200. The method 300 may further include an act 308 of loading the PCD elements substantially as described above regarding the act of loading 208 of method 200. Optionally, the act 308 of loading the PCD elements may include loading the PCD elements 102 and 104 to failure or fracture of one or both PCD elements. In an embodiment, the loading technique employed in act 308 may be face to face compressive loading, wherein the PCD elements are opposing and at least partially overlap each other. In an embodiment, at least a portion of the face to face contact of the first PCD element and the second PCD element may be leached surface to leached surface, wherein PCD tables 122 and 124 include the opposing leached surfaces and/or regions. The method 300 includes an act 309 of observing at least one event substantially as described above regarding the act of observing at least one event 209 of method 200.

The method 300 further includes an act 310 of characterizing the relative strength and/or durability of one or both of the PCD elements. Optionally, such characterizing may be based on at least load at failure. In an embodiment, the relative strength of a PCD element may be characterized by additionally using at least area of overlap of the PCD elements. In an embodiment, the method 300 may include in act 310 using at least one acoustic emission observed during loading to characterize the relative strength of a PCD element. Such characterization may be substantially as described above regarding the method 200 and/or below regarding method 500. In an embodiment, the method 300 may include in act 310 using at least optical data observations made during an event to characterize the relative strength and/or durability of a PCD element substantially as described above regarding method 200 and/or below regarding the method 500. In an embodiment, the act 310 may include using at least photo-elastic stress patterns observed during loading to characterize the relative strength of a PCD element substantially as described above regarding method 200.

The act 310 of characterizing the relative strength and/or durability of one or both of the PCD elements may additionally include correlating the determined relative strength to one or more PCD element characteristics or manufacturing characteristics. PCD element characteristics may include one or more of, PCD table thickness, PCD table to substrate proportion, PCD table density, PCD table porosity, PCD grain size, metal solvent catalyst composition, PCD composition, or combinations thereof. PCD element manufacturing characteristics may include one or more of sintering temperature, sintering pressure, leaching characteristics, leaching time, leaching process parameters, leaching agent composition, leaching agent concentration, or combinations thereof. The foregoing PCD element characteristics or manufacturing characteristics are not intended to be limiting or an exhaustive list thereof.

Direct comparisons of load characteristics, including one or more of load during failure, duration under load, load ramp rate, an integrated load versus counts curve, etc., may be made between superabrasive elements exhibiting different characteristics (e.g., any of those characteristics listed above) to at least partially determine the relative strength of a superabrasive element compared to a different superabrasive element. For example, a superabrasive element having a thicker PCD table may exhibit a lower failure point under load (e.g., relative strength) than a superabrasive element having a thinner PCD table. In such an embodiment, the comparison may indicate that a thinner PCD table, for a specific composition of diamond, exhibits a greater load strength. In an embodiment, as a means of quality control, a comparison of load characteristics for a specific composition may be made between identical or substantially similar superabrasive elements to determine if a particular production batch meets an expected standard for that composition.

The method 300 further includes an act 312 including adjusting one or more process parameters for fabricating a PCD element responsive to at least the determined relative strength from act 310. The act 312 of adjusting one or more process parameters may include adjusting, by way of non-limiting example, the PCD table thickness, the PCD table to substrate proportion, the diamond powder and resulting grain size, the sintering pressure, the sintering temperature, the cementing constituent (e.g., cobalt) to carbide ratio in the substrate, or combinations of the foregoing. Such adjustments to process parameters may result in adjustment of catalyst concentration, internal stress, the extent of diamond-to-diamond bonding, the relative strength, or combinations of the foregoing, in the resulting PCD element. In act 312, one or more process parameters of act 302 may be adjusted, such as adjusting, for example, the precursor diamond powder average particle size, composition, or diamond powder distribution (e.g., thickness); metal-solvent catalyst presence, type, or concentration; the HPHT process parameters such as sintering pressure or sintering temperature; the finishing process; the leaching process such as leaching agent, leaching agent composition, leaching process parameters, leaching agent concentration, or leaching time; or any combination of the foregoing. By tailoring, for example, the average diamond particle size, PCD table thickness, PCD table to substrate proportion, sintering pressure, sintering temperature, or cobalt presence, increased wear resistance and relative strength may be increased as compared to similarly fabricated PCDs where the same process parameter was not adjusted. Additionally, by controlling the metal-solvent catalyst concentration in the PCD element so it is sufficiently low and/or controlling HPHT process conditions to impart a high-degree of diamond-to-diamond bonding in the PCD element (for a given diamond particle formulation), the PCD element may exhibit one or more improved performance characteristics. Performance characteristics may include increased wear resistance, increased relative strength (e.g., reduced cracking), improved thermal stability, or combinations of the foregoing. Explaining further, reducing catalyst in a sintered PCD element may reduce damage and thermal degradation and/or increase abrasion resistance during use.

For example, at elevated temperature and in the presence of a metal-solvent catalyst, some of the diamond grains in the PCD element may undergo a chemical breakdown or back-conversion to graphite via interaction with the metal-solvent catalyst. At very high temperatures, portions of the diamond grains may transform to carbon monoxide, carbon dioxide, graphite, or combinations thereof, causing degradation of the mechanical properties of the PCD table during use.

In an embodiment, the method 300 may be repeated one or more times. For example, a second set of PCD elements 102 and 104 fabricated according to an adjusted manufacturing process may be positioned as in act 306, loaded as in act 308, observed as in act 309, and the relative strength and/or durability of one or both of the new PCD elements 102 and 104 may be characterized according to act 310 using at least a maximum load during or before total failure or fracture (e.g., complete separation, cracking or spalling) of overlapping portions of one or both PCD elements 102 and 104 as a parameter. Further, if desired or needed, the manufacturing process used to fabricate one or both of the PCD elements may be further adjusted according to act 312 substantially as described above.

In an embodiment, fixturing is configured to constrain movement of the superabrasive elements 102 and 104 to the axis of loading 110 (e.g., parallel to the axis of loading) during the act of loading 208, 308 or 508. It will be appreciated by those having skill in the art that suitable fixturing may have many forms and that the following is only a sample embodiment of a fixture and is not intended as a limitation of possible embodiments of suitable fixtures.

Referring now to FIGS. 4A-4C, an embodiment of a fixture 400 for loading the superabrasive elements is disclosed. The fixture 400 may include a first die 402 having a recessed pocket 412 cut therein on an upper surface 472, the recessed pocket 412 being positioned off center in the first die 402 and having substantially the same shape as the first superabrasive element 102. In an embodiment, the cross-section of the recessed pocket 412 may be larger than the first superabrasive element 102 to allow the first superabrasive element 102 to fit into the recessed pocket 412. In another embodiment, the increase in size of the recessed pocket 412 may be such that the first superabrasive 102 may fit into the recessed pocket 412 by interference fit, shrink fit, press fit, or a fit which limits lateral movement of the first superabrasive element 102 in the recessed pocket 412. The recessed pocket 414 may be sized and configured as described herein with respect to recessed pocket 412. In an embodiment, the recess 412 or 414 may be of sufficient depth to allow a portion of the superabrasive element 102 or 104 to protrude out of the recessed pocket 412 or 414. In an embodiment, a superabrasive element 102 or 104 may be secured in a fixture 400 by bonding the superabrasive element 102 or 104 to the fixture 400. Optionally, bonding may take place inside of the recessed pocket 412. The first die 402 may further include at least one shaft recess 452 formed on the upper surface 472, to a depth suitable to hold a shaft 422. The first die 402 may further include at least one bearing recess 462 formed on the upper surface 472, to a depth suitable to hold a sleeve bearing 432. Optionally, other linear bearings may be used.

The fixture 400 further includes a second die 404, formed in the same manner and orientation as the first die 402, such that the second die 404 has a recess 414 formed on an upper surface 474 and at least one shaft recess 454 and at least one bearing recess 464 formed off center on the upper surface 454 of the second die 404. The first die 402 and second die 404 are configured such that when the dies 402 and 404 are generally opposed, the off center recessed pockets 412 and 414 provide a selected overlap for the superabrasive elements 102 and 104 disposed therein. Additionally, the first die 402 and second die 404 are configured such that when the dies 402 and 404 are oriented with the upper surface 472 facing the upper surface 474, the at least one shaft recess 452 and 454 aligns with a corresponding at least one bearing recess 462 or 464 of the counterpart die 402 or 404. The fixture 400 further includes sleeve bearings 432 disposed in the bearing recesses 462 and 464, and shafts 422 disposed in corresponding shaft recesses 452 and 452. The fixture 400 is configured such that a shaft 422 in the shaft recess 452 or 454 in one die 402 or 404, aligns with and fits into the sleeve bearing 432 in the bearing recess 462 or 464 of the opposing die 402 or 404, thereby constraining movement of the dies 402 and 404, in relation to each other, to only the axis of loading 110.

In an embodiment, the shafts 422 are tapped or threaded (e.g., a female or male threaded connection) on the end disposed in the shaft recess 452 or 454. The first die 402 and second die 404 further comprising at least one fastener recess 492 and 494, respectively. The fastener recess 492 and 494 being configured to house a fastener 442, wherein the fastener recesses 492 and 494 are formed on the lower surface 482 and 484 of the first and second dies 402 and 404, and are formed therethrough to a corresponding shaft recess 452 or 454 disposed on the upper surface 472 or 474 of the respective first die 402 or second die 404. Each of the fasteners 442 may be correspondingly threaded or tapped (e.g., male or female threaded connection) and disposed through the lower surface 482 or 484 of the corresponding die and fastened to the threaded end of the shaft 422. The shaft 422 may be disposed through the shaft recess 452 or 454 on the upper surface 472 or 474 of the die 402 or 404, thereby fastening or affixing the shaft 422 in place in the shaft recess 452 or 454 of a die 402 or 404.

In an embodiment, the recessed pockets 412 and 414 may be disposed farther or closer to the center of the respective dies 402 or 404 to increase or decrease the area of overlap A between the first superabrasive element 102 and the second superabrasive element 104. The position of the recessed pockets 412 and 414 may cause the upper surfaces 112 and 114 of the superabrasive elements 102 and 104 to be substantially parallel to one another. In an embodiment, one or both of the recessed pockets 412 or 414 may be formed to create a non-parallel alignment between the upper surface 112 of the first superabrasive element 102 and the upper surface 114 of the second superabrasive element 104, while still maintaining an overlap of the superabrasive elements 102 and 104. In an embodiment, the dies 402 and 404 may be configured to provide an angle between the upper surface 112 of the first superabrasive element 102 and the upper surface 114 of the second superabrasive element 104 of more than zero degrees (0°) and less than ninety degrees (90°). In such an embodiment, the movement of the superabrasive elements 102 and 104 is constrained to the axis of loading 110 as described above. For example, the upper surface 112 of the first superabrasive element 102 may be arranged to contact the upper surface 114 of the second superabrasive element 104 at a forty five degree (45°) contact angle. Such a contact angle may provide different information regarding the desired contact angle or configuration of the PCD element in a drilling apparatus.

In an embodiment, the recessed pockets 412 and 414 may be formed to create substantially parallel alignment between the upper surfaces 112 and 114 of the superabrasive elements 102 and 104, with the plane of contact between the upper surfaces 112 and 114 being non-perpendicular to the axis of loading 110. Put another way, the pockets 412 and 414 may be configured such that the plane of contact between the upper surfaces 112 and 114 of the super abrasive elements 102 and 104 may be at complementary angles of more than zero degrees (0°) and less than ninety degrees (90°) in relation to the upper surface 472 or 474 of the dies 402 and 404 respectively, such that the upper surfaces 112 and 114 are substantially parallel to one another. Such a configuration may provide different information (e.g., information about non-normal compressive force with respect to the opposing surfaces of the PCD elements upon contact between parallel PCD elements) regarding the desired contact angle or configuration of the PCD element in a drilling apparatus.

The fixture 400 is merely one embodiment of a suitable test fixture. Other configurations for fixturing that hold the superabrasive elements to be tested may be employed that depart from the specific details of the fixture 400 without departing from the function or purpose of fixture 400.

Figure 5A:
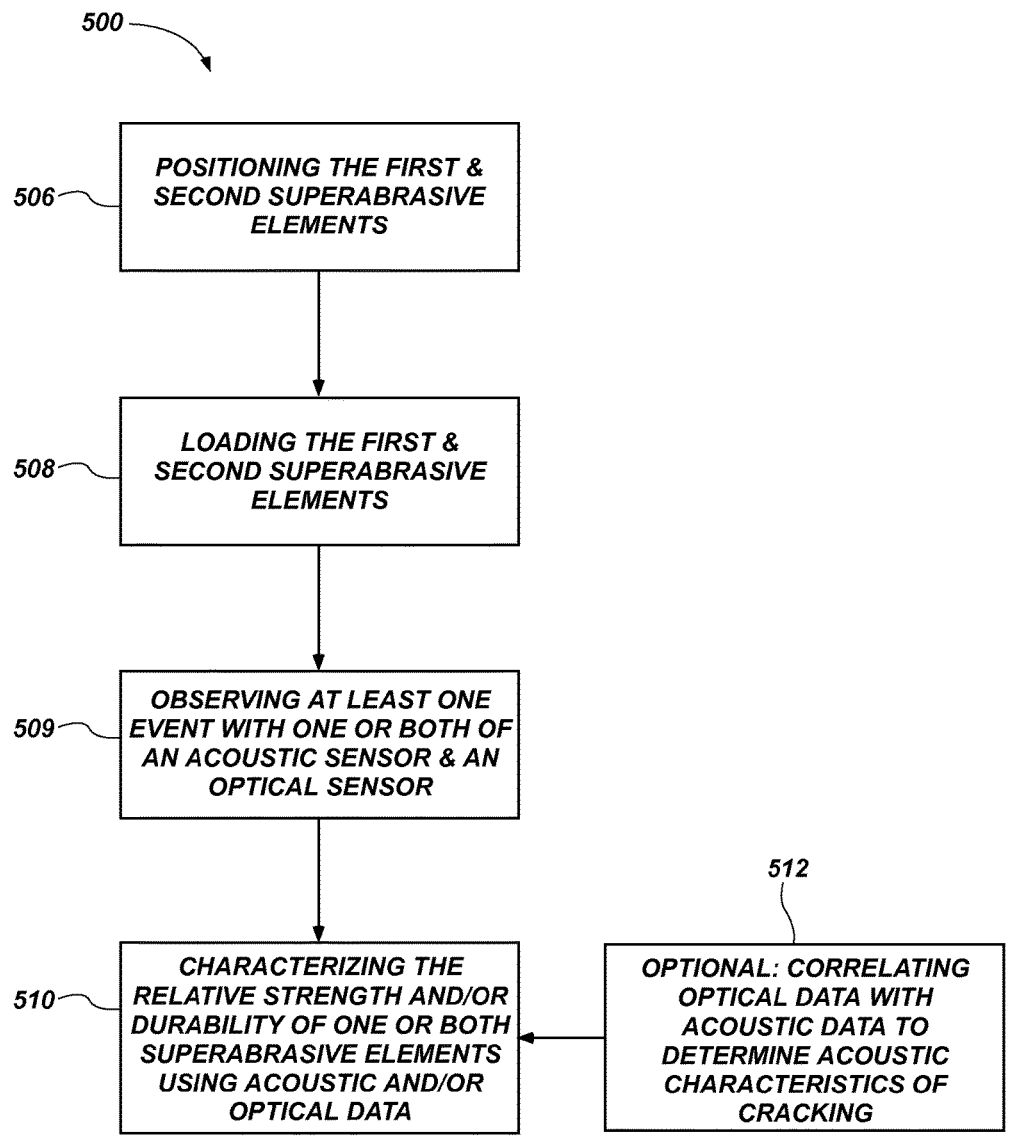
FIG. 5A is a flow diagram illustrating a method for characterizing a relative strength of a superabrasive element, according to an embodiment.
Figure 5B:
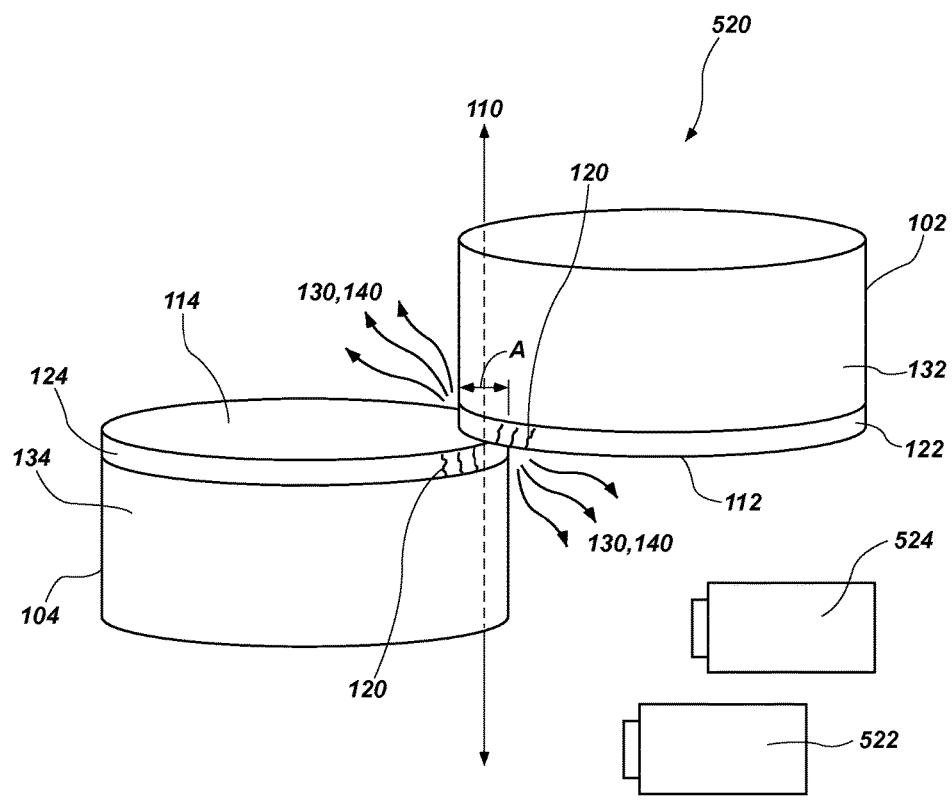
FIG. 5B is a schematic diagram of an acoustic emission and optical data recording apparatus configured to measure and record the acoustic emissions and optical data generated during an event, according to an embodiment.

FIG. 5A is a flow diagram a method 500 for characterizing the relative strength and/or durability of a superabrasive element by observing at least one of acoustic emissions or optical data produced during loading or when the superabrasive element is under a load. In an embodiment, the method 500 includes an act of positioning 506 substantially as described above regarding the act 206. The method 500 further includes an act of loading 508 substantially as described above regarding the act of loading 208 and 308. The method 500 further includes an act of observing and/or sensing 509 at least one event using an acoustic sensor 522 or optical sensor 524. The acoustic sensor 522 may be configured to at least one of observe, sense, or detect acoustic emissions 130 produced during at least one event. For example, the acoustic sensor 522 may be a suitable acoustic transducer configured to sense acoustic emissions. The optical sensor 524 may be configured to at least one of observe, sense, or detect visual signs of an event (e.g., visual cracking or spalling), or invisible signs of an event (e.g., infrared emissions). The at least one acoustic sensor 522 may be used to record one or more acoustic emissions, or the optical sensor 524 (e.g., a high speed camera capable of detecting visible or non-visible light) may be used to record optical data produced during the at least one event. Optical data may include energy emissions 140 or visual signs of cracking 120 on the superabrasive elements 102 and/or 104. The method 500 may further include an act 510 of characterizing the relative strength and/or durability of one or both of superabrasive elements 102 and 104 using at least one of the detected acoustic emissions and/or optical data produced during at least one event. In an embodiment, the act of characterizing the relative strength and/or durability of one or both of superabrasive elements 102 and 104 may additionally include using a maximum load during or before an event (e.g., failure or fracture of at least one of the superabrasive elements) as a parameter.

In an embodiment, the act of observing 509 includes using the acoustic sensor 522 to observe and/or record acoustic emissions produced during an event. Acoustic emissions observed during an event may be associated with cracking in a superabrasive element. Each acoustic emission 130 produces a dynamic signal including, by way of non-limiting example, frequency, wavelength, duration, rise time, counts (the number of peaks above a threshold value in a discrete acoustic emission), and amplitude. As shown in FIG. 5B, the acoustic sensor 522 may be configured to observe/record the acoustic emissions 130 produced by one or more of the superabrasive elements 102 and 104 under load. The acoustic sensor 522 may observe and/or record a single acoustic emission or series of acoustic emissions 130 throughout an event, such as for example, the graph depicted in FIG. 5C. For example, the acoustic sensor 522 may be an acoustic transducer configured to sense acoustic emissions. The number of acoustic emissions 130 may be counted to determine the total number of acoustic emissions ("counts" or individually a "count"). In an embodiment, the counts may be the total number of wavelength peaks of an acoustic emission above a selected threshold level for the acoustic emission. In an embodiment, counts may be the number of discrete acoustic emissions observed/recorded during a given interval. In this manner, counts may represent damage (e.g., cracking or fracturing) accumulation.

Figure 5C:
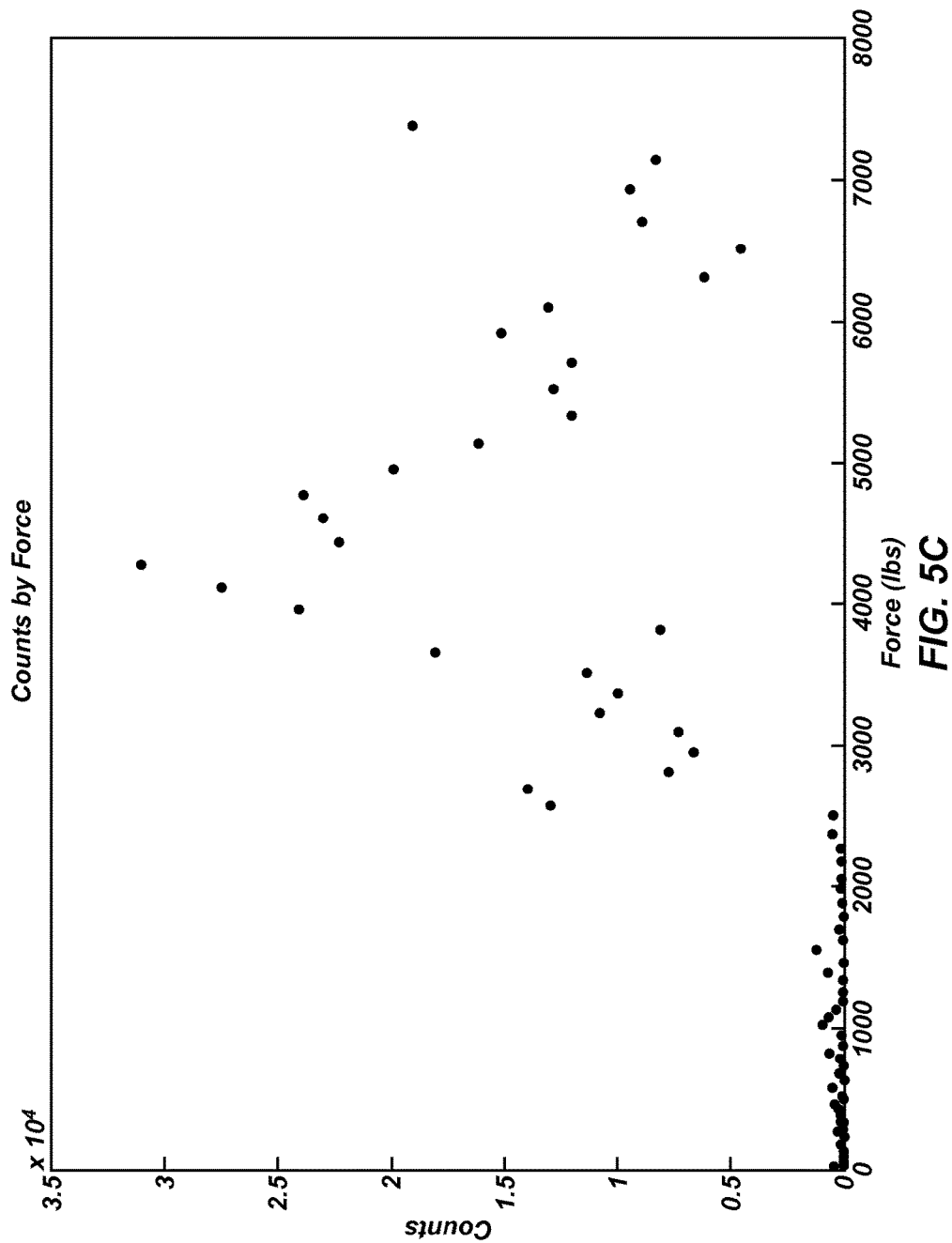
FIG. 5C is a graph of acoustic emission counts as a function of force during compressive loading according to an embodiment.
Figure 5D:
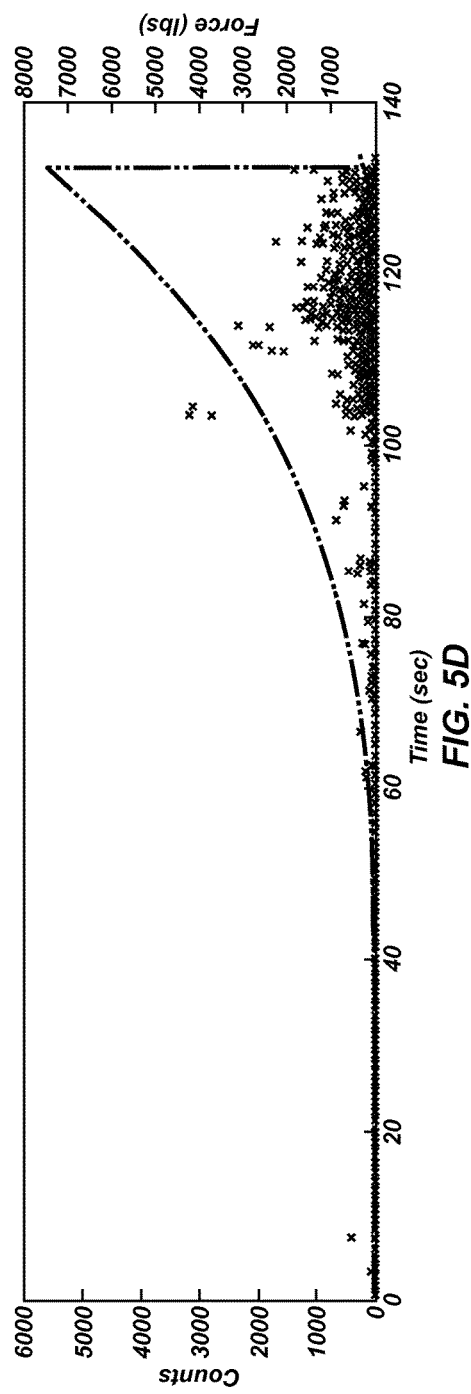
FIG. 5D is a graph of acoustic emission counts as a function of time and force during compressive loading according to an embodiment.
Figure 5E:
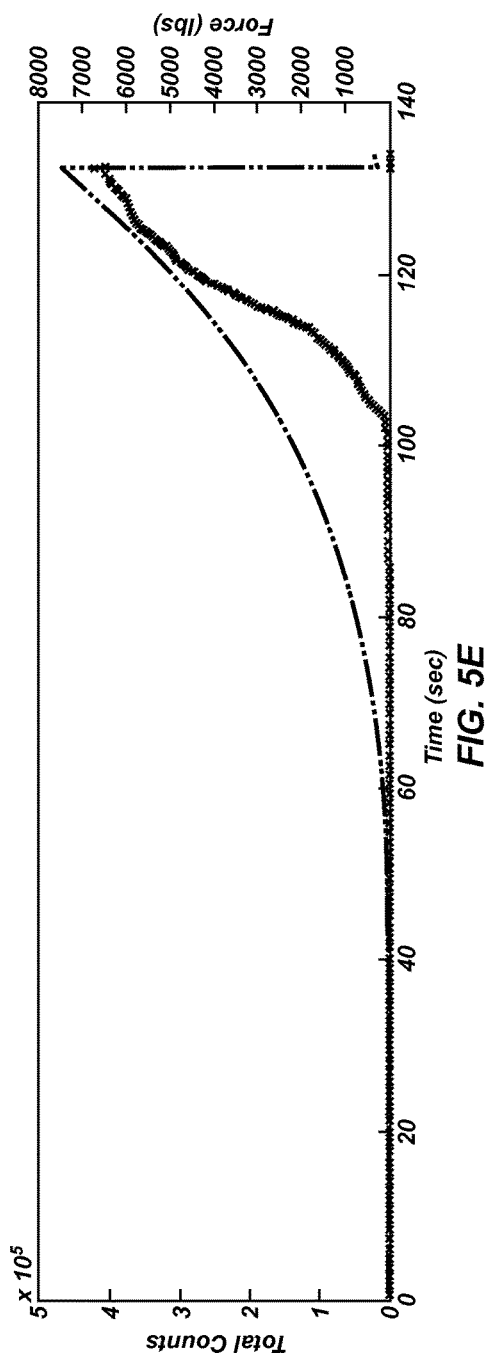
FIG. 5E is a graph of total acoustic emission counts as a function of time and force during compressive loading according to an embodiment.

In an embodiment, observed and/or recorded acoustic emissions may be correlated to the load (e.g., ramped or unramped load) used at a specific time and/or event during loading in order to build a load versus acoustic emission graph such as any of those depicted in FIGS. 5C-5E. The load versus acoustic emission graph may account for, by way of example, the number of acoustic emissions at or near a selected load and/or at a selected point in time during loading as shown in FIGS. 5C and 5D, the total number of acoustic emissions produced or observed up to a point in time or up to an applied amount of load during the loading process (e.g., total damage accumulation) as shown in FIG. 5E, amplitudes (e.g. maximum or average amplitude) of acoustic emission up to or at a given load, or combinations thereof. For example, the load versus acoustic emission graph substantially as depicted in FIG. 5C or 5D may be used to produce and/or determine the load versus acoustic emission curve depicted in FIG. 5E, which may be used to calculate the relative strength of the tested superabrasive element. Relative strength or durability of the superabrasive element may be determined using at least a load versus acoustic emission graph or curve in a number of ways.

In an embodiment, the load versus acoustic emission graph, such as that depicted in FIGS. 5C and/or 5D, may be used to evaluate relative strength at a selected load based on acoustic emissions at that specific load, time, or load and time. In an embodiment, the relative strength and or durability of the superabrasive element 102 or 104 may be determined by the number of counts observed up to a specific load amount, the load at occurrence of the first count, or as explained below integrating an area under the curve defined by the points plotted on a load versus acoustic emission graph. In an embodiment, the relative strength or durability of the superabrasive element 102 or 104 may be determined by integrating the area under a load versus acoustic emission curve based on total acoustic emission counts at (e.g., up to) a point during loading, such as that depicted in FIG. 5E. The determined relative strength or durability value may be compared to experimentally determined values for superabrasive elements of different compositions or made using different methods of manufacture. For example, the larger the value determined from integrating the area under the load versus acoustic emission curve prior to total failure of the superabrasive element, the stronger the relative strength or durability of the superabrasive element. In an embodiment, the determined strength or durability value may be used to correlate or predict strength, performance or durability of the tested superabrasive element based on comparison to previously determined experimentally determined values for other superabrasive elements. In an embodiment, the acoustic emission data in the load versus acoustic emission curve may be based on the counts observed at a specific load and/or time (FIG. 5D). In an embodiment, the determined relative strength of a superabrasive element may be used to adjust fabrication process parameters. In an embodiment, the relative strength of the tested superabrasive element may be used to perform quality control on a given superabrasive element or batch of superabrasive elements fabricated under the same process parameters. In an embodiment, the amplitude or frequency acoustic emissions at a specific load may indicate the relative strength or durability of the superabrasive element. For example, lower amplitude or frequency acoustic emissions may be indicative of a stronger superabrasive element than higher amplitude or frequency emissions.

In an embodiment, as shown in FIG. 5B, the act of recording 509 includes using an optical sensor 524, which may include a high speed camera or one or more photodiodes, to record a visual record of at least one upper surface 112 or 114 during an event. An embodiment may include an optional act 512 of correlating (e.g., synchronizing) the optical data with acoustic emission data to correlate specific visual signs of failure with specific acoustic emissions 130 produced during loading to further characterize and identify which acoustic emissions 130 correspond to certain failure modes and/or events. For example, a large acoustic emission 130 may be correlated with a large crack forming in the superabrasive element. In an embodiment, acoustic emissions 130 may be used to predict type and/or extent of failure in a superabrasive element 102 or 104, based at least in part on the character (e.g., amplitude or frequency) of the acoustic emissions 130 observed during loading.

In an embodiment, the act of observing 509 may include using the optical sensor 524 which may include a light detecting array to record energy emissions 140 (e.g., visible light emissions) produced in one or both superabrasive elements 102 and 104 during a failure event. The light detecting array may be configured to record single or multiple wavelengths of light, including by way of non-limiting example, one or more of ultraviolet light, visible light, or infrared light. The light detecting array may be configured to record energy emissions 140 produced by one or more of the superabrasive elements 102 and 104 under load. The light detecting array may record a single light emission or series of energy emissions 140 during loading. In an embodiment, energy emissions 140 may be used to predict type and extent of failure in a superabrasive element 102 or 104, based at least in part on the character (e.g., amplitude or frequency) of the energy emissions 140 observed during loading. In some embodiments, the optical sensor 524 may include an electromagnetic energy detector to detect photons, particles emissions, electromagnetic radiation (e.g., electromagnetic waves), etc. In some embodiments, the electromagnetic energy emissions 140 may be used to predict type and extent of failure in the superabrasive element 102 or 104, based at least in part on the character of the electromagnetic energy emissions 140 observed during loading. The observed or recorded energy emissions 140 may be used to characterize the relative strength and/or relative durability of the superabrasive element in an identical or substantially similar way as any described herein. For example, an energy emission 140 count may be used to build a load versus energy emission graph or curve, which may be used in the same way as the load versus acoustic emission graph or curve described herein. As another example, the one or more of a specific detected wavelength, amplitude, or frequency of the energy emission 140 may be correlated to the relative strength or durability of the superabrasive element. For example, lower amplitude energy emissions may indicate a stronger superabrasive element at a specific load.

Referring now to FIG. 5B, a schematic illustration of an apparatus for characterizing the relative strength of a superabrasive element using acoustic emissions and/or an optical sensor record produced during a failure event is shown. In an embodiment, the apparatus 520 includes superabrasive elements opposing and overlapping each other which can be loaded substantially as described above regarding FIG. 1A. The superabrasive elements may be held in a fixture such as fixture 400 (not shown here). The apparatus 520 further includes an acoustic sensor 522, configured to detect and record acoustic emissions 130 produced during loading. The apparatus 520 further includes an optical sensor 524; such optical sensor 524 may comprise a high speed camera configured to capture visual images of the superabrasive element 102 and/or 104 during loading. In an embodiment the optical sensor 524 may include a light detecting array or electromagnetic energy detector, configured to detect and record energy emissions (e.g., light) 140 produced during loading. The acoustic sensor 522 and/or optical sensor 524 may be positioned in any configuration which allows for effective detection and/or recording of acoustic emissions, visual data, and/or light emissions produced during loading. In an embodiment, as shown in FIG. 5B, the position of the acoustic sensor 522 and/or the optical sensor 524 may be at least partially defined by extending a plane defined by the surface of overlap between the superabrasive elements 102 and 104, and facing the acoustic sensor 522 and/or the optical sensor 524, positioned substantially on the plane, and oriented in the direction of the surface of overlap. Put another way, the acoustic sensor 522 and/or the optical sensor 524 may be positioned such that one or both face the area of overlap of the superabrasive elements and are substantially aligned along the plane defined by the overlapping surfaces.

In an embodiment, the optical sensor 524 may include a high speed camera, the high speed camera may be located sufficiently close to the superabrasive elements 102 and 104, during loading, to allow effective detection and recording of visual development of changes (e.g., cracks 120), if any, in the superabrasive elements 102 and 104. In an embodiment, the optical sensor 524 may include a light detecting array. The light detecting array may be located sufficiently close to the superabrasive elements 102 and 104, during loading, to allow effective detection and recording of energy emissions 140 produced from the superabrasive elements 102 and 104 during an event. In an embodiment, one or more of acoustic emissions, visual observations, energy emissions, or amount of applied load and the disclosed methods associated therewith may be used to characterize the relative strength or durability of a superabrasive element.

Applications for PCD Elements and PDCs

The PCD elements and PDCs that have been characterized and/or fabricated as described above may be used in a number of different applications including, but not limited to, use in a rotary drill bit, a thrust-bearing apparatus, a radial bearing apparatus, a subterranean drilling system, or a wire-drawing die. The various applications discussed above are merely some examples of applications in which the PCD elements and PDCs may be used. Other applications are contemplated, such as, by non-limiting example, by employing the disclosed characterized PCD elements and PDCs in friction stir welding tools.

Figure 6A:
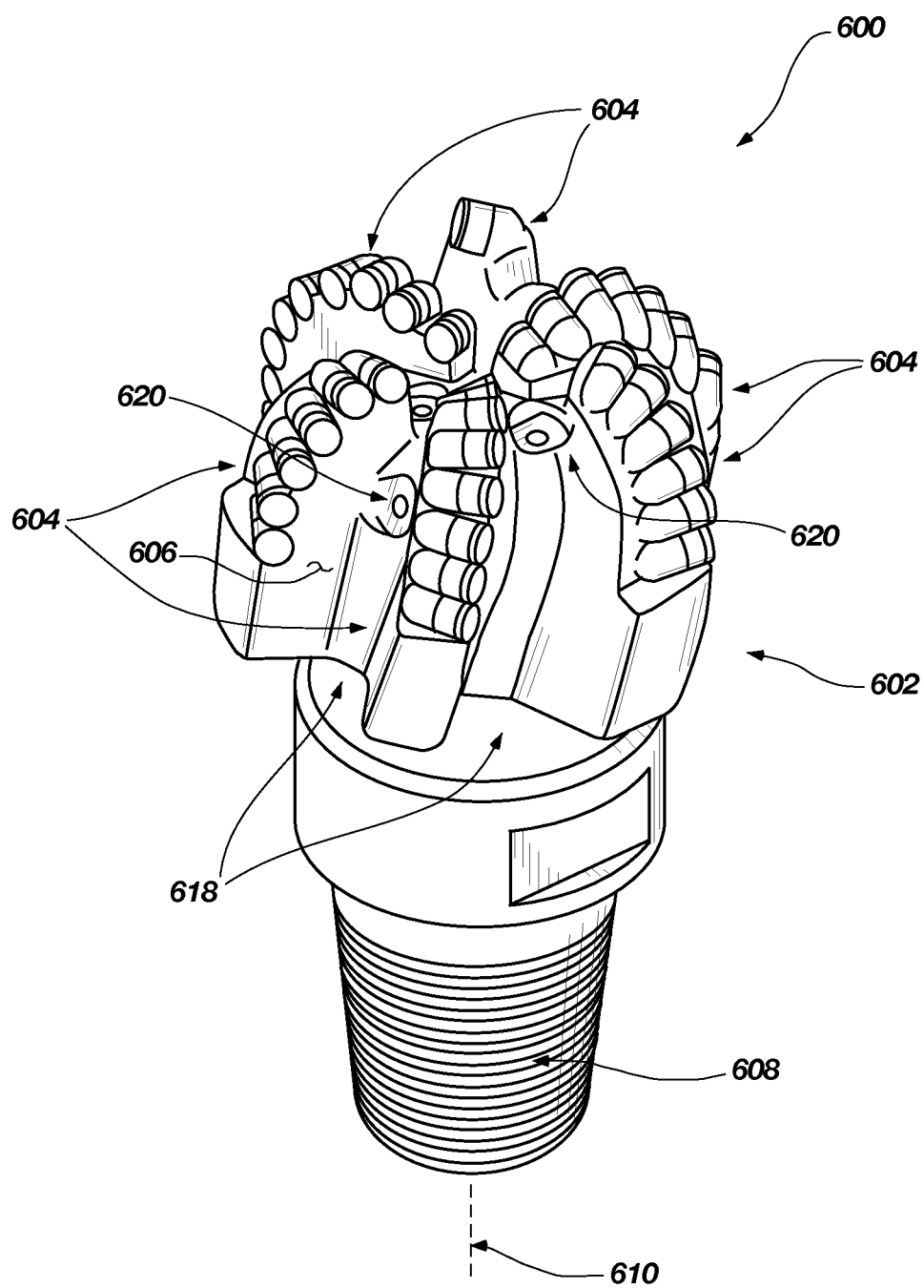
FIG. 6A is an isometric view of an embodiment of a rotary drill bit employing one or more of the superabrasive elements characterized the methods disclosed herein.
Figure 6B:
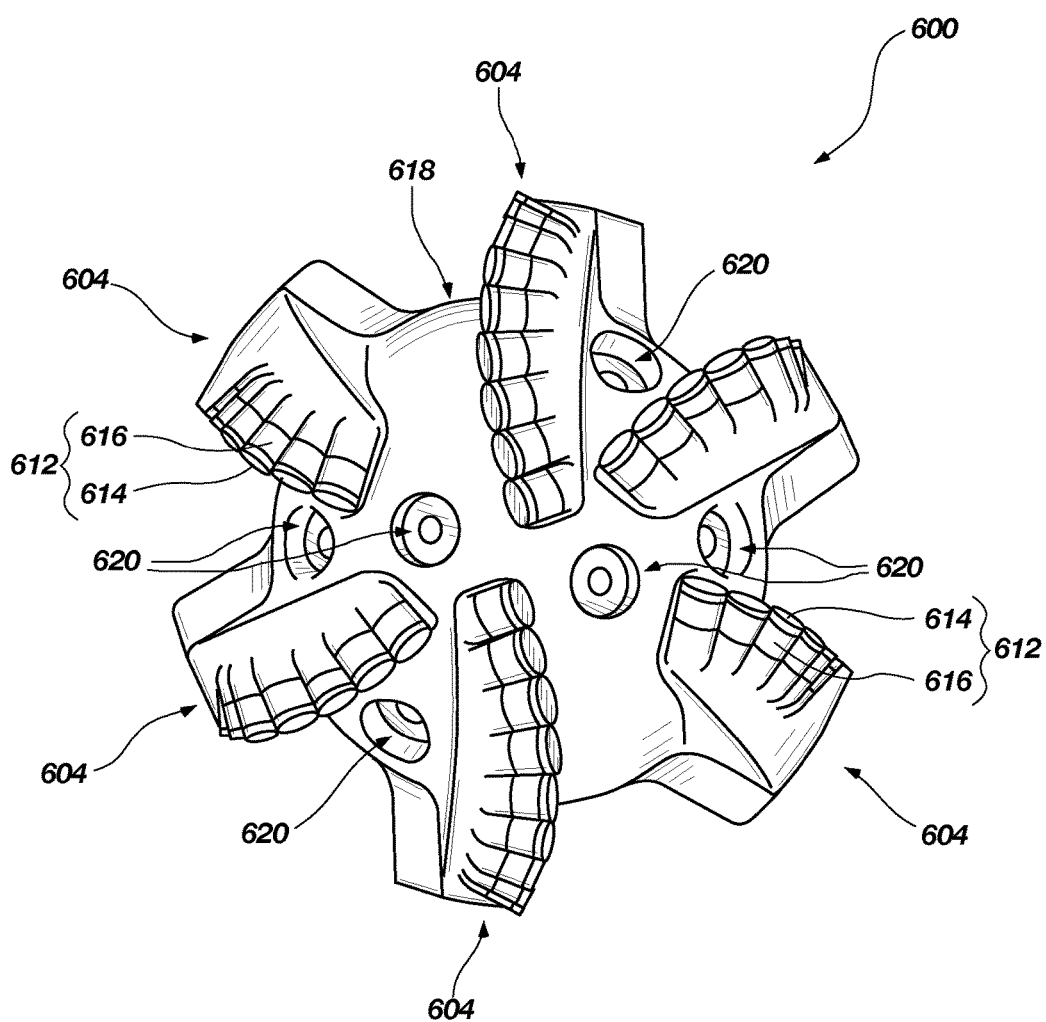
FIG. 6B is a top view of the rotary drill bit shown in FIG. 6A.

FIG. 6A is an isometric view and FIG. 6B is a top elevation view of an embodiment of a rotary drill bit 600. The rotary drill bit 600 includes at least one PDC configured according to any of the previously described PDC embodiments. The rotary drill bit 600 comprises a bit body 602 that includes radially and longitudinally extending blades 604 with leading faces 606, and a threaded pin connection 608 for connecting the bit body 602 to a drilling string. The bit body 602 defines a leading end structure for drilling into a subterranean formation by rotation about a longitudinal axis 610 and application of weight-on-bit. At least one PDC element may be affixed to the bit body 602. With reference to FIG. 6B, a plurality of PDCs 612 are secured to the blades 604. For example, each PDC 612 may include a PCD table 614 bonded to a substrate 616. Also, circumferentially adjacent blades 604 define so-called junk slots 618 therebetween, as known in the art. Additionally, the rotary drill bit 600 may include a plurality of nozzle cavities 620 for communicating drilling fluid from the interior of the rotary drill bit 600 to the PDCs 612.

FIGS. 6A and 6B merely depict an embodiment of a rotary drill bit that employs at least one cutting element comprising a PDC, without limitation. The rotary drill bit 600 is used to represent any number of earth-boring tools or drilling tools, including, for example, core bits, roller-cone bits, fixed-cutter bits, eccentric bits, bicenter bits, reamers, reamer wings, or any other downhole tool including PDCs, without limitation.

Embodiments of PCD elements and/or PDCs fabricated or characterized as disclosed herein may be used in any apparatus or structure in which at least one conventional PCD or PDC is typically used. The embodiments of PCD elements and/or PDCs disclosed herein may also form all or part of heat sinks, wire dies, bearing elements, cutting elements, cutting inserts (e.g., on a roller-cone-type drill bit), machining inserts, or any other article of manufacture as known in the art. In an embodiment, a rotor and a stator, assembled to form a rotary or thrust-bearing apparatus, may each include one or more PCD elements and/or PDCs characterized, fabricated, and/or configured according to any of the embodiments disclosed herein and may be operably assembled to a downhole drilling assembly. U.S. Pat. Nos. 4,410,054; 4,560,014; 5,364,192; 5,368,398; and 5,480,233, the disclosure of each of which is incorporated herein, in its entirety, by this reference, disclose subterranean drilling systems within which bearing apparatuses utilizing the PCD elements and/or PDCs disclosed herein may be incorporated. Other examples of articles of manufacture that may use any of the PCD elements and/or PDCs disclosed herein are disclosed in U.S. Pat. Nos. 4,811,801; 4,268,276; 4,468,138; 4,738,322; 4,913,247; 5,016,718; 5,092,687; 5,120,327; 5,135,061; 5,154,245; 5,180,022; 5,460,233; 5,544,713; and 6,793,681, the disclosure of each of which is incorporated herein, in its entirety, by this reference.

WORKING EXAMPLES

The following working examples provide further detail in connection with the specific embodiments described above.

Working Example 1

A plurality of PDCs were each manufactured according to the following process or a substantially similar process, using substantially similar materials resulting in substantially similar PDCs. A layer of diamond powder was disposed on a cobalt-cemented tungsten carbide substrate. The layer of diamond particles and the cobalt-cemented tungsten carbide substrate were HPHT processed in a high pressure cubic press at a minimum temperature of about 1400° C. and a cell pressure of about 5-5.5 GPa to form a PDC comprising a PCD table integrally formed and bonded to the cobalt-cemented tungsten carbide substrate. The PCDs were mounted in a fixture substantially as described regarding FIGS. 4A-C, resulting in opposing and overlapping PDCs. A load frame was used to apply up to 3000 pounds of load to the PCDs until failure occurred (exhibited in this example by a sharp drop in load). The relative strength of the PCDs was characterized by dividing the load at failure by the area of overlap of the PCDs. The larger the value, the larger the relative strength or durability of the PDC.

Working Example 2

PDCs were formed according to the process described in working example 1. The PCDs were loaded according to the process described above for working example 1. Testing included using an acoustic sensor to record acoustic emissions produced during loading. A count of acoustic emissions exceeding a threshold value, as discrete events, was recorded. A graph of load versus corresponding acoustic emissions was made to produce a load versus acoustic emission curve. The curve exhibited an endpoint denoted by a sharp drop in load (e.g., point of total or complete failure of the PCD). The area under the load versus acoustic emission curve was integrated to calculate a value characterizing the relative strength of the PDC tested. PDCs with larger values are believed to have greater relative strength.

Working Example 3

PDCs were formed according to the process described in working example 1. The PCD's were loaded according to the process described above for working example 1. An acoustic sensor was used to observe and record acoustic emissions produced during loading. A count of acoustic emissions as discrete events was recorded. A graph of load versus the sum of total acoustic emissions up to that load and point in time was made to produce a load versus total acoustic emission curve. The area under the load versus acoustic emission curve was integrated to give a relative strength for the PDC tested. The load versus total emissions curve was also compared to a load as a function of time graph to demonstrate under which conditions during loading more or less events occur.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A method of characterizing a relative strength of a superabrasive element, the method comprising:
positioning a first superabrasive element having a first superabrasive table bonded to a first substrate, the first superabrasive table defining a first upper surface, and a second superabrasive element having a second superabrasive table bonded to a second substrate, the second superabrasive table defining a second upper surface, so that the first and second upper surfaces defined by the first and second superabrasive tables are at least partially overlapping and facing each other to define an area of overlap therebetween;
loading, along an axis of loading, the first superabrasive element and the second superabrasive element against each other while overlapped such that the first upper surface of the first superabrasive table is forced against the second upper surface of the second superabrasive table;
observing, during the act of loading, at least one failure event in either one or both of the first and second superabrasive elements; and
characterizing the relative strength of the one or both of the first and second superabrasive elements based at least partially on the at least one failure event;
wherein movement of the first superabrasive element and movement of the second superabrasive element are fixtured to be constrained to directions parallel to the axis of loading throughout the acts of loading and observing.

2. The method of claim 1 wherein positioning a first superabrasive element having a first superabrasive table and a second superabrasive element having a second superabrasive table so that the first and second upper surfaces of the first and second superabrasive tables are facing each other to define an overlap includes placing the first superabrasive element and the second superabrasive element in a fixture to constrain the movement of the first superabrasive element and the movement of the second superabrasive element to the directions parallel to the axis of loading, wherein the axis of loading is located in the area of overlap.

3. The method of claim 1 wherein characterizing the relative strength of the one or both superabrasive elements further includes at least partially basing the relative strength on a ratio of a load applied during the loading to the area of overlap.

4. The method of claim 1, further comprising adjusting at least one superabrasive element fabrication parameter based on at least the characterization of the relative strength.

5. The method of claim 1 wherein the first superabrasive element and the second superabrasive element are different sizes.

6. The method of claim 1 wherein the first superabrasive element and the second superabrasive element include one or more of a substantially identical geometry or composition.

7. The method of claim 1 wherein the first superabrasive element and the second superabrasive element exhibit unequal elastic moduli.

8. The method of claim 1 wherein each of the first superabrasive element and the second superabrasive element includes a polycrystalline diamond ("PCD") table.

9. The method of claim 8 wherein characterizing the relative strength of one or both of the first and second superabrasive elements includes at least partially basing the relative strength characterization on thickness of the PCD table in the first superabrasive element or the second superabrasive element.

10. The method of claim 1 wherein positioning a first superabrasive element having a first superabrasive table and a second superabrasive element having a second superabrasive table so that the first and second upper surfaces of the first and second superabrasive tables are facing each other to define an overlap includes orienting the upper surface of the first superabrasive table to be substantially parallel to the upper surface of the second superabrasive table.

11. The method of claim 1, further comprising:
   recording at least one acoustic emission produced during loading using an acoustic sensor;
   recording at least one image of one or more of the first and second superabrasive elements during loading using an optical sensor;
   correlating the at least one acoustic emission and the at least one image to characterize the at least one acoustic emission; and
   characterizing the relative strength of one or both of the first and second superabrasive elements at least partially based on the at least one acoustic emission.

12. The method of claim 1, further comprising:
   recording at least one acoustic emission produced during loading using an acoustic sensor;
   correlating the at least one acoustic emission to an applied load at the time of the at least one acoustic emission; and
   characterizing the relative strength of one or both of the first and second superabrasive elements at least partially based on the correlation of the at least one acoustic emission to the applied load at the time of the at least one acoustic emission.

13. The method of claim 12 wherein characterizing the relative strength of one or both of the first and second superabrasive elements at least partially based on the at least one acoustic emission includes generating a load versus acoustic emission curve and integrating the area under the curve.

14. A method of characterizing a relative strength of a polycrystalline diamond ("PCD") element, the method comprising:
   positioning a first PCD element having a first PCD table bonded to a first substrate, the first PCD table defining a first upper surface, and a second PCD element having a second PCD table bonded to a second substrate, the second PCD table defining a second upper surface, so that the first and second upper surfaces defined by the first and second PCD tables are at least partially overlapping and facing each other to define an area of overlap therebetween;
   loading, along an axis of loading, the first PCD element and the second PCD element against each other while overlapped with a compressive load such that the first upper surface of the first PCD table is forced against the second upper surface of the second PCD table;
   observing, during the act of loading, at least one failure event in either one or both of the first and second PCD elements; and
   characterizing the relative strength of the one or both of the first and second PCD elements based at least partially on one or more observations made during the at least one failure event;
   wherein movement of the first PCD element and movement of the second PCD element are fixtured to be constrained to directions parallel to the axis of loading throughout the acts of loading and observing.

15. The method of claim 14 wherein at least one of the first PCD table and the second PCD table is at least partially leached.

16. The method of claim 14 wherein characterizing the relative strength of the one or both of the first and second PCD elements further includes dividing a load applied during the loading by the area of overlap.

17. The method of claim 14 wherein characterizing the relative strength of the one or both of the first and second PCD elements further includes determining a relative strength value for the one or both of the first and second PCD elements,
   the method further comprising comparing the determined relative strength value for the one or both of the first and second PCD elements with one or more relative strength values for other PCDs.

18. The method of claim 14 wherein observing at least one failure event includes recording at least one acoustic emission produced during loading using an acoustic sensor and the method further includes:
   correlating the at least one acoustic emission to an applied load at a time of the at least one acoustic emission; and
   characterizing the relative strength of one or both of the first and second PCD elements at least partially based on the correlation of the at least one acoustic emission to the applied load at the time of the at least one acoustic emission.

19. The method of claim 18 wherein characterizing the relative strength of one or both of the first and second PCD elements at least partially based on the correlation of the at least one acoustic emission to the applied load at the time of the at least one acoustic emission includes generating a load versus acoustic emission curve and integrating an area underneath the load versus acoustic emission curve to determine a relative strength value.

20. The method of claim 18, further comprising adjusting at least one PCD element fabrication parameter based on at least the characterization of the relative strength.

21. A method of characterizing a relative strength of a superabrasive compact element, the method comprising:
   positioning a first superabrasive element having a first superabrasive table bonded to a first substrate, the first superabrasive table defining a first upper surface, and a second superabrasive element having a second superabrasive table bonded to a second substrate, the second superabrasive table defining a second upper surface, so that the first and second upper surfaces defined by the first and second superabrasive tables are overlapping and facing each other to define an area of overlap therebetween;
   applying a compressive load, along an axis of loading, to the first superabrasive element and the second superabrasive element while overlapped such that the first upper surface of the first superabrasive table is forced against the second upper surface of the second superabrasive table;

producing, during the act of applying a compressive load, at least one failure event in one or both of the first and second superabrasive elements;

sensing at least one light emission produced during the application of the compressive load using a light detecting array;

sensing an applied load during the at least one light emission; and characterizing the relative strength of the one or both of the first and second superabrasive elements at least partially based on the at least one light emission and the applied load corresponding thereto;

wherein movement of the first superabrasive element and movement of the second superabrasive element are fixtured to be constrained to directions parallel to the axis of loading throughout the acts of applying a compressive load and producing at least one failure event in one or both of the first and second superabrasive elements.

22. The method of claim 21 wherein characterizing the relative strength of the one or both of the first and second superabrasive elements at least partially based on the at least one light emission and the applied load corresponding thereto includes making a load versus light emission curve and integrating the area underneath the curve to determine a relative strength value.

\* \* \* \* \*